(12) United States Patent
Sano et al.

(10) Patent No.: US 10,568,529 B2
(45) Date of Patent: Feb. 25, 2020

(54) FLOW RATE CONTROL VALVE AND BLOOD PRESSURE INFORMATION MEASUREMENT APPARATUS

(71) Applicant: OMRON HEALTHCARE CO., LTD., Muko-shi, Kyoto (JP)

(72) Inventors: Yoshihiko Sano, Kyoto (JP); Ryoichi Fukui, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 16/189,377

(22) Filed: Nov. 13, 2018

(65) Prior Publication Data

US 2019/0076029 A1    Mar. 14, 2019

Related U.S. Application Data

(63) Continuation of application No. PCT/JP2017/016349, filed on Apr. 25, 2017.

(30) Foreign Application Priority Data

May 31, 2016    (JP) .................................. 2016-108589

(51) Int. Cl.
*A61B 5/0235*    (2006.01)
*F16K 31/06*    (2006.01)
(Continued)

(52) U.S. Cl.
CPC ............ *A61B 5/0235* (2013.01); *F16K 31/06* (2013.01); *H01F 7/06* (2013.01); *H01F 7/121* (2013.01);
(Continued)

(58) Field of Classification Search
CPC ......... A61B 5/0235; H01F 7/06; H01F 7/121; H01F 7/16; H01F 2007/086; F16K 31/06
(Continued)

(56) References Cited

U.S. PATENT DOCUMENTS 1,587,921 A  *  6/1926  Ray ..................... F16K 31/0658
                                                    137/339
3,232,312 A  *  2/1966  Lansky ............... F16K 31/0606
                                                    137/315.03
(Continued)

FOREIGN PATENT DOCUMENTS

| JP | H02-131405 U | 11/1990 |
|----|-------------|---------|
| JP | H04-88575 U | 7/1992 |
| JP | 2014-55607 A | 3/2014 |

OTHER PUBLICATIONS

Jul. 11, 2017, International Search Report issued in Patent Application No. PCT/JP2017/16349.

*Primary Examiner* — John Bastianelli
(74) *Attorney, Agent, or Firm* — Oliff PLC

(57) ABSTRACT

A flow rate control valve includes a bobbin and a plunger. On an inner circumferential surface of the bobbin, multiple protruding regions that extend in a direction parallel in an axial direction to the plunger, and a plurality of recessed grooves that form flow paths for a fluid when valve is open are provided side by side alternatingly in a circumferential direction. The multiple recessed grooves include a first recessed groove, second recessed groove, and third recessed groove that are arranged side by side sequentially in the circumferential direction. An interval in the circumferential direction between the first recessed groove and second recessed groove and an interval in the circumferential direction between the second recessed groove and third recessed groove are the same. Surfaces of the multiple protruding regions formed on the inner circumferential surface of the bobbin can be arranged at positions closer to those of one perfect circle.

8 Claims, 8 Drawing Sheets

(51) Int. Cl.
- *H01F 7/121* (2006.01)
- *H01F 7/16* (2006.01)
- *H01F 7/06* (2006.01)
- *H01F 7/08* (2006.01)

(52) U.S. Cl.
CPC ......... *H01F 7/16* (2013.01); *H01F 2007/086* (2013.01)

(58) Field of Classification Search
USPC ................ 251/129.15, 129.21; 335/261, 279
See application file for complete search history.

(56) References Cited

U.S. PATENT DOCUMENTS

| | | | | |
|---|---|---|---|---|
| 4,346,847 | A * | 8/1982 | Rissi | F02M 51/0685 |
| | | | | 239/585.2 |
| 6,959,907 | B2 * | 11/2005 | Hironaka | B60T 8/363 |
| | | | | 251/129.07 |
| 7,095,304 | B2 * | 8/2006 | Sano | A61B 5/0235 |
| | | | | 251/129.15 |
| 2007/0120081 | A1 | 5/2007 | Huang | |
| 2014/0166914 | A1 * | 6/2014 | Pott | F16K 31/0665 |
| | | | | 251/129.15 |

* cited by examiner

FLOW RATE CONTROL VALVE AND BLOOD PRESSURE INFORMATION MEASUREMENT APPARATUS

TECHNICAL FIELD

The present invention relates to a flow rate control valve capable of variably controlling a flow rate of a fluid, and a blood pressure information measurement apparatus including such a flow rate control valve.

BACKGROUND ART

Measuring blood pressure information is important for keeping track of the health state of a measurement subject. Various types of blood pressure information can be measured by using a blood pressure information measurement apparatus. A blood pressure information measurement apparatus includes a cuff, and a pressure pump and discharge valve are used as a pressure increase/reduction mechanism for increasing and reducing the internal pressure of the cuff. In a closed state, the discharge valve maintains the internal pressure of a fluid bladder whose pressure has been increased by the pressure pump, and in an open state, the discharge valve reduces the pressure.

A flow rate control valve can be suitably used as the discharge valve. The flow rate control valve includes a movable shaft and a valve body that opposes an outflow port. The valve body is provided at an end portion of the movable shaft. When the internal pressure of the cuff is to be reduced, the outflow flow rate can be controlled by variably controlling the distance between the outflow port and the valve body using the variable shaft. This kind of flow rate control valve largely comes in two types: linear and solenoid.

The solenoid type includes a plunger (movable iron core) serving as a movable shaft, a core (fixed iron core) provided with an outflow port, and a solenoid coil, and the plunger is moved using the solenoid coil. Unlike the linear type, the solenoid type does not require a permanent magnet and has a simple configuration and thus can be made lighter and smaller, and thus the solenoid type is advantageous in that the manufacturing cost is easily reduced.

JP 2014-055607A (Patent Literature 1) discloses a solenoid-type flow rate control valve. This flow rate control valve includes a core provided with an outflow port, a bobbin, a plunger arranged inside of the bobbin, and a valve body provided at an end portion of the plunger so as to oppose the outflow port. If the valve body is in contact with the core, the outflow port is closed by the valve body. If the valve body is separate from the core, air is discharged to the outside of the flow rate control valve via a gap between the inner circumferential surface of the bobbin and the outer circumferential surface of the plunger.

JP H02-131405U (Patent Literature 2) discloses a utility model relating to a gas flow valve. This gas flow valve includes a housing having a cylindrical shape and a valve body arranged inside of the housing. A recess is provided inside of the housing. One side of the recess has a linear shape, and when the valve body is inserted into the housing, a gap is formed between the inner wall (linear portion) of the housing and the valve body. This gap functions as a gas flow path, and according to Patent Literature 2, there may be one, two, three, or more of these gas flow paths.

CITATION LIST

Patent Literature

Patent Literature 1: JP 2014-055607A
Patent Literature 2: JP H02-131405U

SUMMARY OF INVENTION

Technical Problem

In the flow rate control valve, the outflow port opens and the outflow path (cross-sectional area of the flow path) of the fluid gradually expands due to the valve body and the plunger separating from the core, and the fluid is discharged via the gap between the inner circumferential surface of the bobbin and the outer circumferential surface of the plunger. If this gap is made larger, the discharge flow rate (cross-sectional area of the flow path of the fluid) increases, and for example, rapid air discharge can be realized. However, there is concern that if the gap between the inner circumferential surface of the bobbin and the outer circumferential surface of the plunger is made too large, the plunger will be less likely to be held by the bobbin, and rattling of the plunger or the like will be incurred.

In contrast to this, by providing a recessed groove in the inner circumferential surface of the bobbin, the space formed inside of the recessed groove can be utilized as a flow path for discharging the fluid. Since the plunger can be held by the outer surface of the region of the inner circumferential surface of the bobbin in which the recessed groove is not provided (hereinafter also referred to as a protruding region), it is possible to prevent rattling of the plunger and the like from being incurred.

If multiple recessed grooves are provided on the inner circumferential surface of the bobbin, multiple protruding regions are formed on the inner circumferential surface of the bobbin as a result. The plunger is held by the surfaces of the multiple protruding regions. In order to make it possible for the plunger to move stably (with little rattling) inside of the bobbin, ideally, the surfaces of the multiple protruding regions are preferably formed so as to be located on one perfect circle (in other words, so as to conform to one circumferential direction with the same radius).

The inventors of the present invention found that if multiple recessed grooves are provided on the inner circumferential surface of the bobbin, the surfaces of the multiple protruding regions therebetween are sometimes formed such that they are not located on one perfect circle, but are located on one ellipse, for example. In such a case, it is more difficult for the plunger to move stably (with little rattling) inside of the bobbin, and thus the manner in which the valve body comes into contact with the outflow port tends to vary.

If the manner in which the valve body comes into contact with the outflow port varies, variation will occur in the timing at which the outflow port opens when the valve body and the plunger are separate from the core, and in the degree to which the outflow path of the fluid widens. Even if a flow rate control valve is operated with the same control conditions, variation will occur to such an extent that the internal pressure of the cuff decreases, and it is conceivable that different characteristics will be displayed each time measurement is performed.

The seal surface of the valve body for sealing the outflow port and the outflow port provided on the core are not necessarily produced according to a design, and frequently include a manufacturing error in some cases. As disclosed in Patent Document 1, there are also cases in which the seal surface of the valve body is inclined. In these cases, if the manner in which the valve body comes into contact with the outflow surface changes, more significant variation will occur in the timing at which the outflow port opens and in the degree to which the outflow path of the fluid widens.

The present invention was made in view of the above-described circumstances, and aims to provide a flow rate control valve including a structure in which surfaces of multiple protruding regions can be arranged at positions closer to those of one perfect circle even if multiple recessed grooves are provided in the inner circumferential surface of a bobbin, and a blood pressure information measurement apparatus including such a flow rate control valve.

Solution to the Problem

A flow rate control valve according to the present invention is a flow rate control valve capable of variably controlling a flow rate of a fluid, including: a solenoid coil for generating a magnetic flux; a bobbin around which the solenoid coil is wound; a plunger that is arranged inside of the bobbin and is configured to move in an axial direction due to the magnetic flux formed by the solenoid coil; a core in which an outflow port through which the fluid is to pass is formed; and a valve body that is provided at an end portion of the plunger so as to oppose the outflow port, and is configured to open and close the outflow port by separating from and coming into contact with the core, wherein on an inner circumferential surface of the bobbin, a plurality of protruding regions that extend in a direction parallel to the axial direction of the plunger and a plurality of recessed grooves that form flow paths for the fluid when the valve is open are provided side by side alternatingly in a circumferential direction, the plurality of recessed grooves include a first recessed groove, a second recessed groove, a third recessed groove, and a fourth groove that are arranged side by side sequentially in the circumferential direction, an interval in the circumferential direction between the first recessed groove and the second recessed groove, an interval in the circumferential direction between the second recessed groove and the third recessed groove, and an interval in the circumferential direction between the third recessed groove and the fourth recessed groove are the same, the plurality of recessed grooves further include a fifth recessed groove formed between the first recessed groove and the fourth recessed groove, an outer circumferential surface of the plunger includes a circumferential surface region that extends in a circumferential direction, and an engagement region that extends in a direction parallel to the axial direction of the plunger and has a flat surface shape, and in a state in which the plunger is arranged inside of the bobbin, the engagement region opposes a pair of the protruding regions located on both sides of the fifth groove in the circumferential direction, and the plunger is prevented from rotating inside of the bobbin due to the engagement region and the pair of the protruding regions engaging with each other.

In the above-described flow rate control valve, preferably, the widths in the circumferential direction of the first recessed groove, the second recessed groove, and the third recessed groove are the same.

In the above-described flow rate control valve, preferably, groove depths in a radial direction of the first recessed groove, the second recessed groove, the third recessed groove, and the fourth recessed groove are the same.

The above-described flow rate control valve preferably further includes a frame having a pair of side walls, wherein the bobbin and the plunger are arranged between the pair of side walls, and if a straight line that is orthogonal to the pair of side walls and passes through an axial center of the bobbin is drawn, the protruding region is arranged at a position intersecting the straight line.

In the above-described flow rate control valve, preferably, the plunger includes a small diameter portion inside of which the valve body is arranged, and a large diameter portion that is arranged on a side opposite to the side on which the valve body is arranged with respect to the small diameter portion, in the axial direction, and the engagement region is provided only in the large diameter portion.

In the above-described flow rate control valve, preferably, the engagement region is provided only on a portion in the axial direction of the large diameter portion.

A blood pressure information measurement apparatus based on the present invention includes the above-described flow rate control valve as a discharge valve for reducing internal pressure of a compression fluid bladder for compressing a living body.

In the above-described blood pressure information measurement apparatus, preferably, if the flow rate control valve is provided in a main body of the blood pressure information measurement apparatus, in a state in which the main body is placed on a horizontal placement surface, one of the plurality of protruding regions of the flow rate control valve is located lower than all of the recessed grooves in a gravity direction.

Advantageous Effects of the Invention

According to the above-described configuration, it is possible to arrange the surfaces of multiple protruding regions at positions closer to those of one perfect circle due to the interval between the first recessed groove and the second recessed groove being the same as the interval between the second recessed groove and the third recessed groove, among the intervals in the circumferential direction between the multiple recessed grooves.

DESCRIPTION OF EMBODIMENTS

Figure 1:
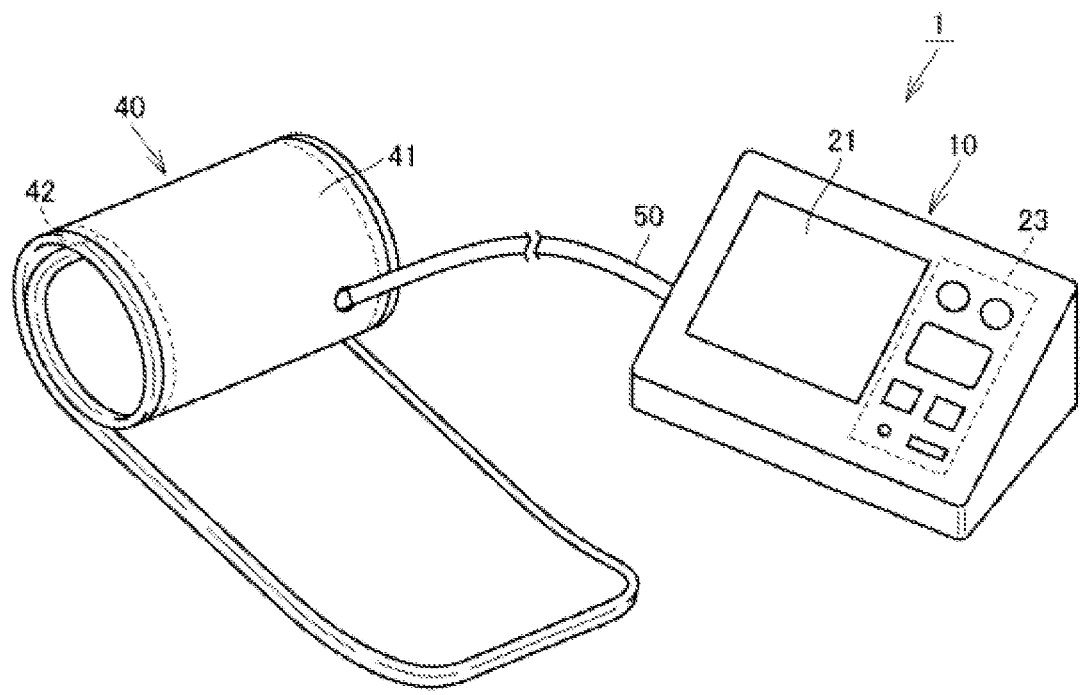
FIG. 1 is a perspective view showing an external structure of a blood pressure monitor of Embodiment 1.

Hereinafter, a flow rate control valve and a blood pressure information apparatus according to an embodiment will be described in detail with reference to the drawings. In the embodiments described below, portions that are the same or are used in common are denoted by the same reference numerals in the drawings, and description thereof is not repeated in some cases.

The embodiments below are described based on a so-called upper-arm-type blood pressure monitor that is configured to be able to measure a systolic blood pressure value and a diastolic blood pressure value of a measurement subject due to a cuff being used while attached to an upper arm of the measurement subject. A flow rate control valve will be described based on an embodiment of being included in this kind of upper-arm-type blood pressure monitor.

However, the technical idea relating to the flow rate control valve disclosed hereinafter is not limited to an upper-arm blood pressure monitor, and can be applied to a wrist-type blood pressure monitor, a foot-type blood pressure monitor, or a blood pressure measurement apparatus that measures average blood pressure values, an oxygen saturation level, and the like. The idea relating to the flow rate control valve disclosed below can be applied also to the field of soft robotics, in which an object is held using suction and discharge of a fluid, or other fields.

Embodiment 1
Blood Pressure Monitor 1

A blood pressure monitor 1 (blood pressure information measurement apparatus) and a flow rate control valve 100A of Embodiment 1 will be described with reference to FIGS. 1 to 6. FIG. 1 is a perspective view showing an external structure of the blood pressure monitor 1, and FIG. 2 is a diagram showing a configuration of functional blocks of the blood pressure monitor 1.

As shown in FIG. 1, the blood pressure monitor 1 includes a main body 10, a cuff 40, and an air tube 50. The main body 10 includes a display unit 21 and an operation unit 23. The cuff 40 includes an outer cover 41 and a compression air bladder 42. The air tube 50 connects the main body 10 and the cuff 40.

Figure 2:
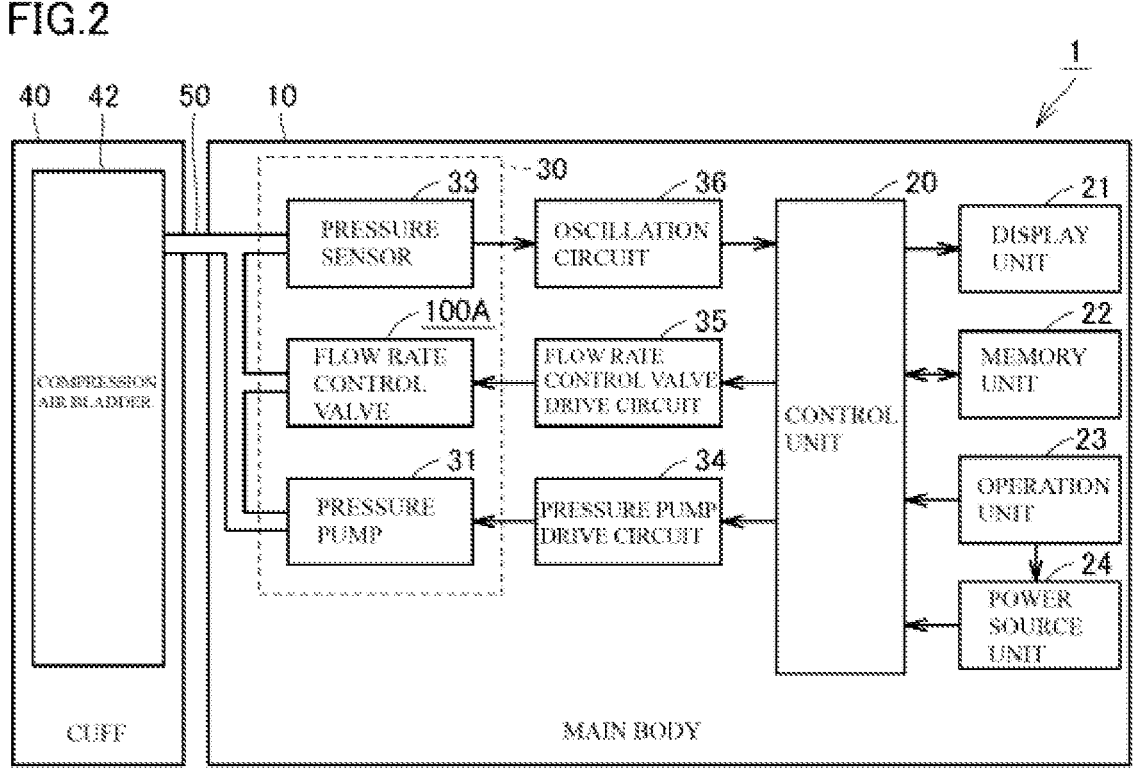
FIG. 2 is a diagram showing a configuration of functional blocks of the blood pressure monitor of Embodiment 1.

As shown in FIG. 2, the main body 10 includes the display unit 21 and the operation unit 23, as well as a control unit 20, a memory unit 22, a power source unit 24, a pressure pump 31, a flow rate control valve 100A, a pressure sensor 33, a pressure pump drive circuit 34, a flow rate control valve drive circuit 35, and an oscillation circuit 36. The pressure pump 31, the flow rate control valve 100A, and the pressure sensor 33 constitute a compression air system component 30, and the pressure pump 31 and the flow rate control valve 100A constitute a pressure increase/reduction mechanism for increasing and reducing the internal pressure of the compression air bladder 42.

The compression air bladder 42 is connected to each of the pressure pump 31, the flow rate control valve 100A, and the pressure sensor 33. The compression air bladder 42 is inflated and swells due to the driving of the pressure pump 31 being controlled, and due to the driving of the flow rate control valve 100A serving as the discharge valve being controlled, the internal pressure is maintained or the compression air bladder 42 is deflated and contracts.

The control unit 20 performs overall control of the blood pressure monitor 1. The display unit 21 displays measurement results and the like. The memory unit 22 stores programs for causing the control unit 20 and the like to execute a processing procedure for blood pressure value measurement, measurement results, and the like. The operation unit 23 inputs instructions from outside to the control unit 20 and the power source unit 24. The power source unit 24 supplies power to the control unit 20 and the like.

The control unit 20 inputs a control signal to the pressure pump drive circuit 34 and the flow rate control valve drive circuit 35, and inputs the measurement results to the display unit 21 and the memory unit 22. The control unit 20 acquires the blood pressure values of the measurement subject based on the pressure values detected by the pressure sensor 33 and inputs the acquired blood pressure values to the display unit 21 and the memory unit 22.

The pressure pump drive circuit 34 controls the operation of the pressure pump 31. The flow rate control valve drive circuit 35 controls the opening and closing operation of the flow rate control valve 100A. The pressure pump 31 is for increasing the internal pressure (hereinafter also referred to as "cuff pressure") of the compression air bladder 42, and is controlled by the pressure pump drive circuit 34.

Due to being controlled by the flow rate control valve drive circuit 35, the flow rate control valve 100A maintains the internal pressure of the compression air bladder 42 and reduces the cuff pressure by releasing the air in the compression air bladder 42 to the outside. The pressure sensor 33 detects the internal pressure of the compression air bladder 42 and inputs an output signal corresponding thereto to the oscillation circuit 36. The oscillation circuit 36 generates a signal with an oscillation frequency corresponding to the signal input from the pressure sensor 33 and inputs the generated signal to the control unit 20.

Flow Rate Control Valve 100A

Figure 3:
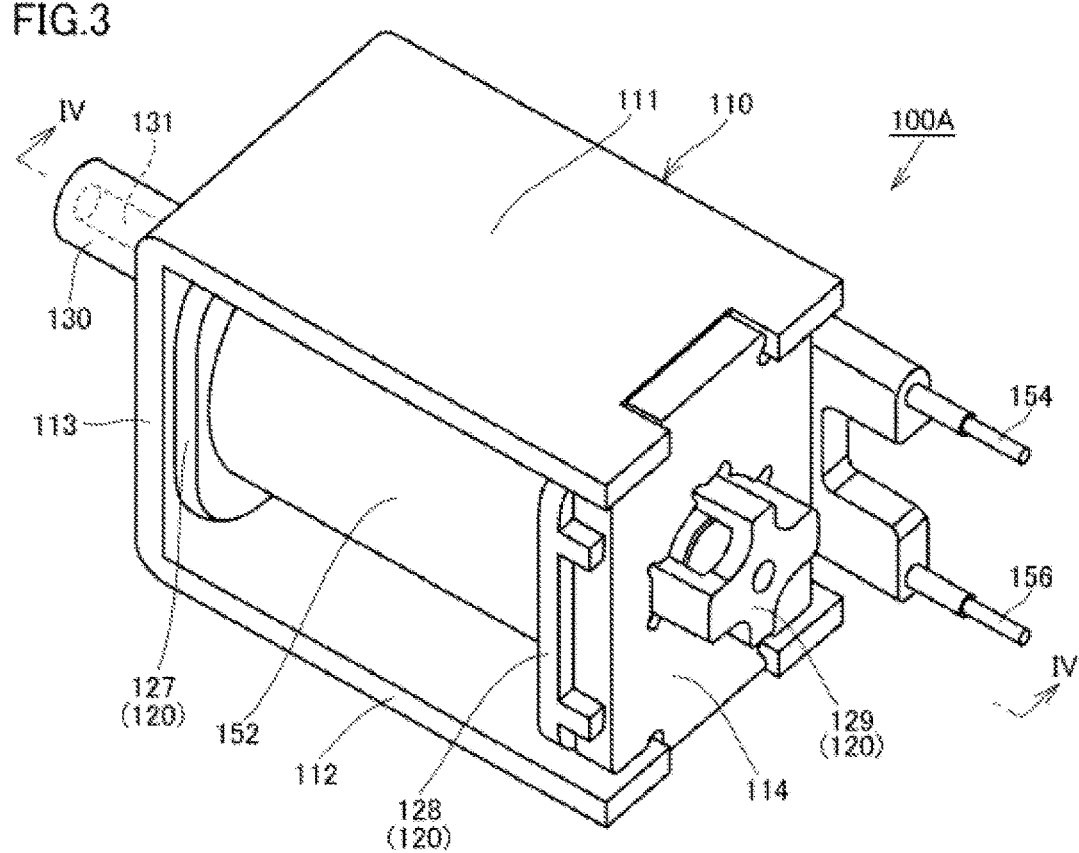
FIG. 3 is a perspective view showing a flow rate control valve of Embodiment 1.
Figure 4:
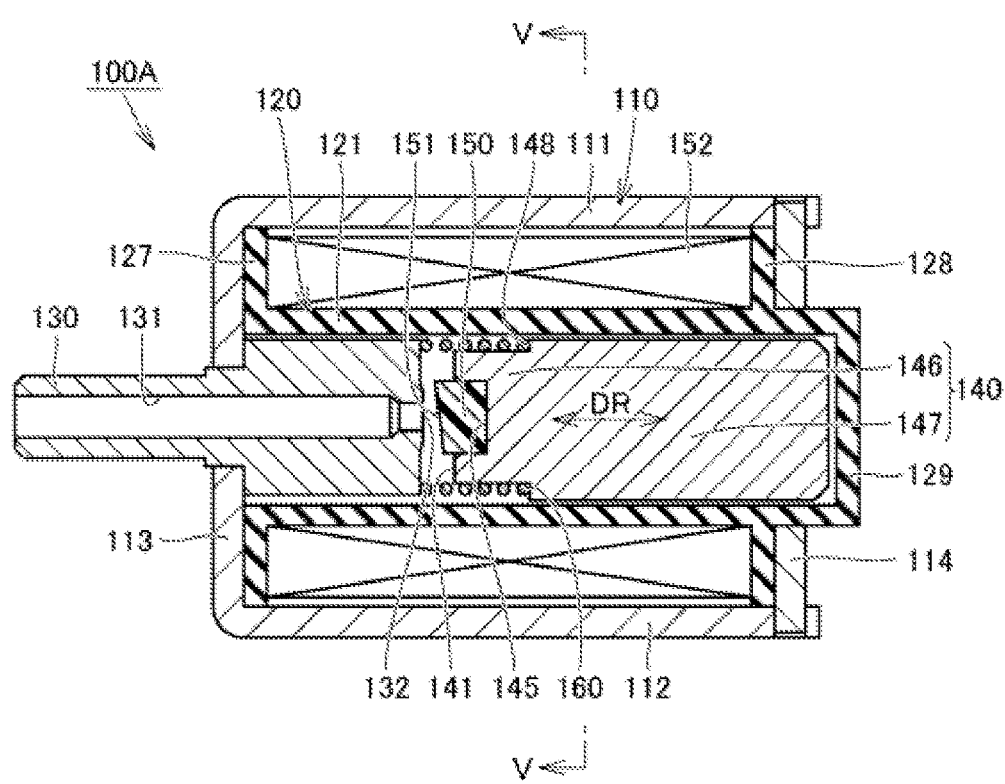
FIG. 4 is a cross-sectional diagram taken along line IV-IV in FIG. 3 and viewed in the direction of arrows.
Figure 5:
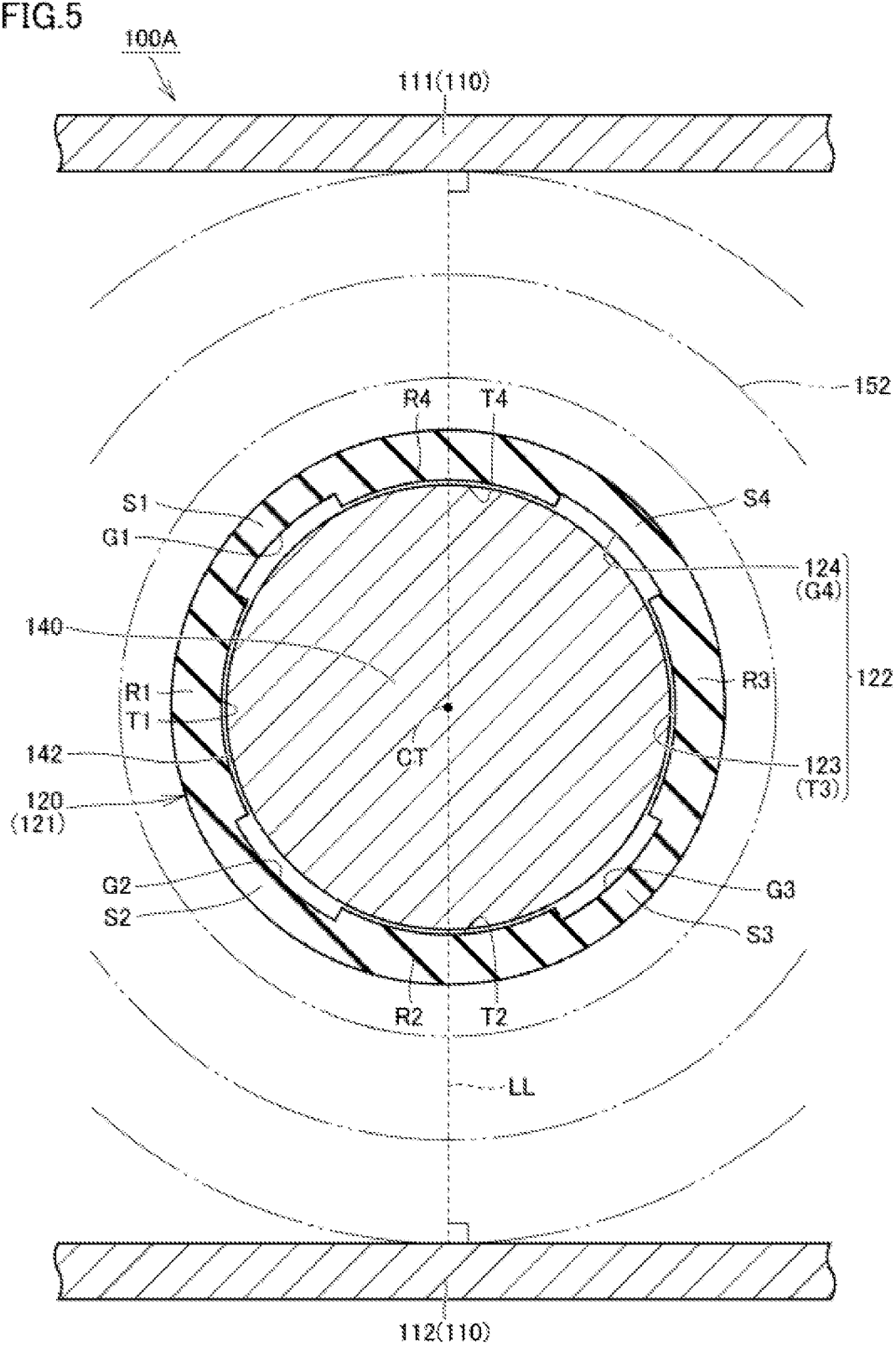
FIG. 5 is a cross-sectional diagram taken along line V-V in FIG. 4 and viewed in the direction of arrows.
Figure 6:
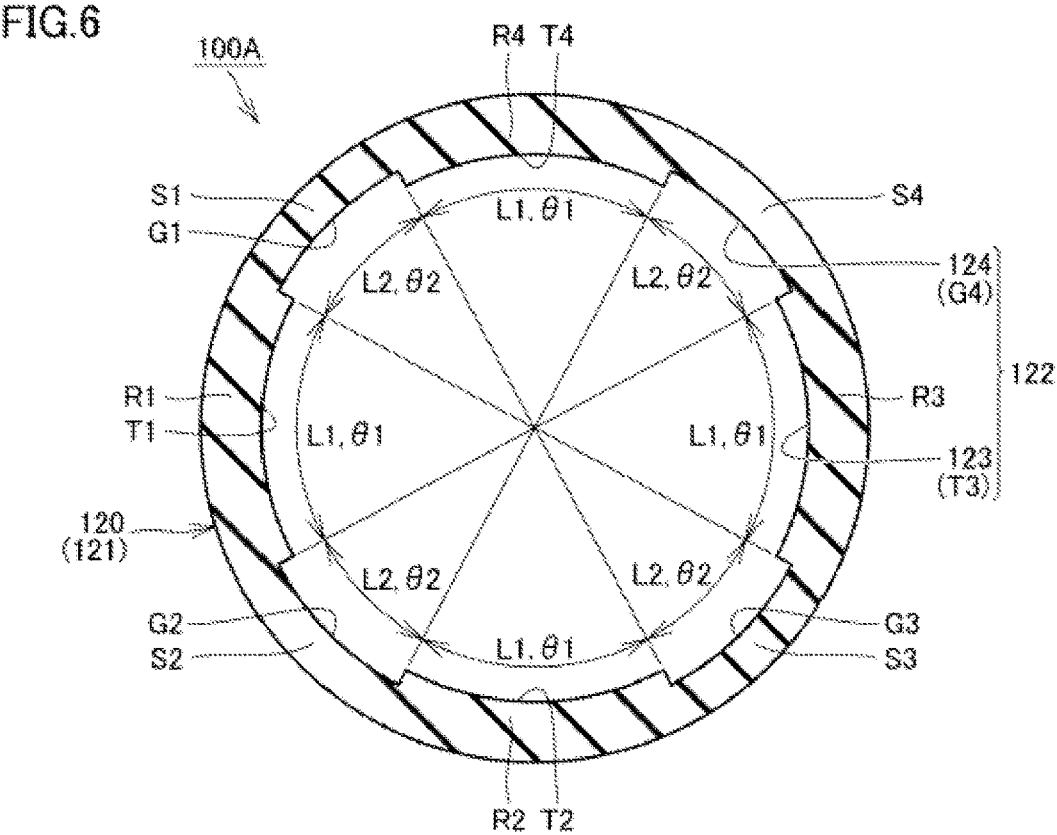
FIG. 6 is a cross-sectional diagram showing a bobbin included in the flow rate control valve of Embodiment 1.

FIG. 3 is a perspective view showing the flow rate control valve 100A. FIG. 4 is a cross-sectional view taken along line IV-IV in FIG. 3 and viewed in the direction of arrows. FIG. 5 is a cross-sectional view taken along line V-V in FIG. 4 and viewed in the direction of arrows. FIG. 6 is a cross-sectional diagram showing a bobbin 120 included in the flow rate control valve 100A.

Mainly referencing FIG. 3, the flow rate control valve 100A has an approximately cuboid shape overall. The flow rate control valve 100A includes a frame 110, a base 114, a bobbin 120 (FIGS. 4 to 6), a core 130, a plunger 140 (FIGS. 4 and 5), a valve body 150 (FIG. 4), a solenoid coil 152, connection terminals 154 and 156, and a spring 160 (FIG. 4).

The frame 110 and the base 114 constitute the outer shell of the flow rate control valve 100A. The frame 110 includes a pair of side walls 111 and 112 that are arranged parallel to each other, and an end wall 113 that connects one end of the side walls 111 and 112. The base 114 connects the other end of the side walls 111 and 112. The base 114 is fixed to the other end of the side walls 111 and 112 through caulking, welding, or the like. The later-described bobbin 120, plunger 140, and solenoid coil 152 are arranged between the pair of side walls 111 and 112 (see FIG. 5).

The frame 110 and the base 114 are constituted by a soft magnetic material (e.g., a magnetic steel plate or a cold-rolled steel plate having a high magnetic permeability). The frame 110 and the base 114 function also as a yoke and adjust the paths of the lines of magnetic force that are generated due to the solenoid coil 152 performing electric conduction.

The bobbin 120 is made of a non-magnetic material (e.g., a resin such as polybutylene terephthalate). The bobbin 120 of the present embodiment includes a cylindrical portion 121 (FIG. 4), a pair of end walls 127 and 128, and a bottom portion 129. The cylindrical portion 121 defines the movement path of the plunger 140 arranged inside of the cylindrical portion 121. The end walls 127 and 128 are both circular ring-shaped.

The end wall 127 is provided at one end in the axial direction (arrow DR) of the cylindrical portion 121, and the end wall 128 is provided at an intermediate portion (portion near the other end) in the same direction of the cylindrical portion 121. The bottom portion 129 is provided so as to close the other end opening of the cylindrical portion 121. The base 114 has an opening, and the other end of the cylindrical portion 121 is arranged so as to go through the opening.

The solenoid coil 152 is wound around the cylindrical portion 121 and is held by the circumferential surface of the cylindrical portion 121 and the end surfaces 127 and 128. Both ends of the solenoid coil 152 are connected to the connection terminals 154 and 156. The solenoid coil 152 generates a magnetic flux due to being supplied with power through the flow rate control valve drive circuit 35 (FIG. 2) and the connection terminals 154 and 156.

The core 130 has a nozzle portion 131 and is fixed through caulking, welding, or the like to the end wall 113 of the frame 110. One end of the nozzle portion 131 forms an outflow port 132 through which the fluid passes, and the outflow port 132 is arranged inside of the cylindrical portion 121 of the bobbin 120. The other end of the nozzle portion 131 is connected to a compression air bladder 42 via the air tube 50 (FIG. 2). Due to the outflow port 132 being opened, the fluid in the compression air bladder 42 is discharged.

The core 130 is constituted by a soft magnetic material (e.g., electromagnetic steel, sulfur composite free-cutting steel, or the like). The core 130 constitutes a fixed iron core, and attracts the plunger 140 due to the magnetic flux passing through when the solenoid coil 152 performs electrical conduction. That is, the flow rate control valve 100A of the present embodiment is a normally-open solenoid-type flow rate control valve in which the outflow port 132 is completely open when not operating.

The plunger 140 has an approximately circular rod shape and is arranged inside of the bobbin 120 (cylindrical portion 121). The plunger 140 is constituted by a soft magnetic material (e.g., electromagnetic steel, sulfur composite free-cutting steel, or the like). The plunger 140 constitutes a movable iron core and moves in the axial direction (arrow DR) by being attracted by the core 130 due to the magnetic flux passing through when the solenoid coil 152 is subjected to electric conduction.

As shown in FIG. 4, the plunger 140 includes a small diameter portion 146 and a large diameter portion 147 that is provided on the side opposite to the side on which the valve body 150 is arranged with respect to the small radius portion 146 in the axial direction (arrow DR). A level difference 148 is provided between the small diameter portion 146 and the large diameter portion 147. A containing recess 145 is provided on the end surface 141 facing the core 130 of the plunger 140 (small diameter portion 146). The containing recess 145 is provided at a position corresponding to the outflow port 132 (a position opposing the outflow port 132), and the valve body 150 is fit into the containing recess 145.

The spring 160 (FIG. 4) is arranged inside of the bobbin 120 (cylindrical portion 121) and is interposed between the core 130 and the plunger 140 in the axial direction (arrow DR). The spring 160 is arranged so as to surround the small diameter portion 146, one end of the spring 160 being in contact with the core 130, and the other end of the spring 160 being in contact with the level difference 148 of the plunger 140. The spring 160 biases the plunger 140 in the direction of moving away from the core 130.

The valve body 150 is provided on the end portion of the plunger 140, and is provided so as to protrude from the end surface 141 in the axial direction. The valve body 150 is constituted by silicone rubber or a nitrile rubber represented by NBR. The valve body 150 is contained in the containing recess 145 provided in the plunger 140. The valve body 150 includes a seal surface 151 and is provided opposing the outflow port 132 provided in the core 130. The valve body 150 is integrated with the plunger 140 and the valve body 150 does not rotate with respect to the plunger 140. The valve body 150 may be fixed to the plunger 140 using an adhesive or the like.

Referencing FIG. 4, when the flow rate control valve 100A is not operating, the solenoid coil 152 is not supplied with power, and thus the magnetic circuit is not formed. The plunger 140 and the valve body 150 are arranged at a position located away from the core 130 due to the biasing force of the spring 160. The air in the compression air bladder 42 that communicates with the nozzle portion 131 is discharged to the space located between the core 130 and the plunger 140 via the outflow port 132, and is further discharged to the outside of the flow rate control valve 100A via a gap (the details of which will be described later) between the inner circumferential surface of the bobbin 120 and the outer circumferential surface of the plunger 140.

When the flow rate control valve 100A is operating, the solenoid coil 152 is supplied with power, thereby forming a magnetic circuit such that a magnetic flux passes through the frame 110, the core 130, the plunger 140, and the base 114. The plunger 140 and the valve body 150 are attracted to the core 130 side against the biasing force of the spring 160.

If the current applied to the solenoid coil 152 is a predetermined amount or greater, the plunger 140 is attracted to the core 130 side to its maximum limit along the axial direction, and the outflow port 132 is closed due to the seal surface 151 of the valve body 150 coming into contact with the core 130. In this state, air is blocked from flowing out via the outflow port 132, and the internal pressure of the compression air bladder 42 is maintained.

If the current applied to the solenoid coil 152 is less than the above-described predetermined amount, the plunger 140 is attracted to the core 130 side in the axial direction to a certain extent. In this state, the seal surface 151 of the valve body 150 does not completely close the outflow port 132, but the outflow port 132 is closed to a certain extent. Although the air flows out through the outflow port 132, the air is blocked to a certain extent from flowing out from the outflow port 132, and thus the outflow flow rate is restricted.

The distance between the outflow port 132 and the seal surface 151 located on the outflow port 132 side of the valve body 150 is variably adjusted by controlling the amount of current applied to the solenoid coil 152. By adjusting the drive current for the flow rate control valve 100A, it is possible to variably adjust the flow rate of compressed air that flows out from the outflow port 132.

Detailed Construction of Plunger 140 and Bobbin 120

Referencing FIGS. 5 and 6, as described above, the plunger 140 (FIG. 5) has an approximately circular column shape, and is arranged inside of the cylindrical portion 121 of the bobbin 120. The outer circumferential surface of the plunger 140 of the present embodiment has a circumferential surface shape. In other words, if the cross-sectional shape of the plunger 140 is viewed in a cross-sectional view taken in a horizontal direction orthogonal to the axial direction (movement direction of the plunger 140), the outer circumferential surface of the plunger 140 has a shape that extends in the circumferential direction about a center of curvature CT (FIG. 5), so as to have approximately the same radius from the center of curvature CT.

When the outflow port 132 opens due to the valve body 150 (FIG. 4) moving away from the core 130, the fluid is discharged via the gap between the inner circumferential surface 122 of the bobbin 120 and the outer circumferential surface 142 of the plunger 140. As stated at the beginning, by providing multiple recessed grooves 124 (FIGS. 5 and 6) on the inner circumferential surface 122 of the bobbin 120, the spaces formed inside of the multiple grooves 124 can be used as paths for discharging the liquid. If the multiple grooves 124 are provided on the inner circumferential surface 122 of the bobbin 120, as a result, the multiple protruding regions 123 are formed on the inner circumferential surface 122 of the bobbin 120.

The multiple (here, four) protruding regions 123 that extend parallel in the axial direction to the plunger 140 and the multiple (here, four) recessed grooves 124 that form flow paths for the liquid when the valve is open are provided side by side alternatingly in the circumferential direction on the inner circumferential surface 122 of the bobbin 120 of the present embodiment. In the present embodiment, a total of four recessed grooves G1, G2, G3, and G4 are included in the multiple recessed grooves 124, and a total of four protruding regions T1, T2, T3, and T4 are included in the multiple protruding regions 123.

The recessed groove G1 (first recessed groove), the recessed groove G2 (second recessed groove), the recessed groove G3 (a third recessed groove), and the recessed groove G4 (a fourth recessed groove) are aligned in the stated order in the circumferential direction, and the protruding regions T1, T2, T3, and T4 are also aligned in the stated order in the circumferential direction. Due to the recessed grooves G1, G2, G3, and G4 being provided in the bobbin 120, the bobbin 120 includes thin portions S1, S2, S3, and S4, which are relatively thinner in the radial direction, and thick portions R1, R2, R3, and R4, which are relatively thicker in the radial direction.

The inner surfaces of the thin portions S1, S2, S3, and S4 each correspond to a groove bottom portion of the recessed grooves G1, G2, G3, and G4. The inner surfaces of the thick portions R1, R2, R3, and R4 each correspond to a top surface portion of the protruding regions T1, T2, T3, and T4. The plunger 140 can be held by the inner surfaces of the thick portions R1, R2, R3, and R4, that is, by the top surface portions of the protruding regions T1, T2, T3, and T4, and therefore it is possible to prevent incurring rattling or the like of the plunger 140.

Referencing FIG. 6, in the present embodiment, an interval L1 in the circumferential direction between the recessed groove G1 and the recessed groove G2 and an interval L1 between the recessed groove G2 and the recessed groove G3 are the same. In other words, in the circumferential direction, the angle range θ1 in which the protruding region T1 (thick portion R1) is provided and the angle range θ1 in which the protruding region T2 (thick portion R2) is provided are the same value.

Action and Effect

As described at the beginning, for example, if multiple recessed grooves G1, G2, and G3 are provided on the inner circumferential surface 122 of the bobbin 120, the surfaces of the protruding regions T1 and T2 therebetween are sometimes formed such that they are not located on one perfect circle, but are located on one ellipse, for example. This tends to happen if the interval L1 in the circumferential direction between the recessed groove G1 and the recessed groove G2 and the interval L1 in the circumferential direction between the recessed groove G2 and the recessed groove G3 are different values. The reason for this is inferred as follows.

The bobbin 120 having the protruding regions T1 and T2 and the recessed grooves G1, G2, and G3 can be produced through molding using a mold, for example. This kind of bobbin 120 has a thick portion R1 at a portion corresponding to the protruding region T1, has a thick portion T1 at a portion R2 at a portion corresponding to the protruding region T2, and has a thin portion S2 at a portion corresponding to the recessed groove G2.

For example, if the bobbin 120 is produced through molding, stress caused by thermal contraction occurs in the thick portions R1 and R2 and the thin portion S2. The interval L1 between the recessed grooves G1 and G2 and the interval L1 between the recessed grooves G2 and G3 being different is synonymous with the width in the circumferential direction of the thick portion R1 and the width in the circumferential direction of the thick portion R2 being different. If the interval L1 between the recessed grooves G1 and G2 and the interval L1 between the recessed grooves G2 and G3 are different, there will be a difference between the thermal contraction force acting on the thick portion R1 located on one side of the thin portion S2 and the thermal contraction force acting on the thick portion R2 located on the other side of the thin portion S2.

If focus is given to the thick portion S2, there will be a difference between the force with which the thick portion R1 located on one side of the thin portion S2 attempts to contract (be displaced) toward the inside in the diameter direction and the force with which the thick portion R2 located on the other side of the thin portion S2 attempts to contract (be displaced) toward the inside in the diameter direction. Due to the presence of this difference in force, it is inferred that the surfaces of the protruding regions T1 and T2 will be formed such that they are not located on one perfect circle, but are located on one ellipse, for example. This is not limited to molding, and it is inferred that it is similar also in the case of providing the multiple recessed grooves G1, G2, and G3 on the inner circumferential surface 122 of the bobbin 120 through cutting or the like, for example.

In the present embodiment, as described above, the interval L1 between the recessed grooves G1 and G2 and the interval L1 between the recessed grooves G2 and G3 are the same. Accordingly, if focus is given to the thick portion S2, there will hardly be any difference between the force with which the thick portion R1 located on one side of the thin portion S2 attempts to contract (be displaced) toward the inside in the diameter direction and the force with which the thick portion R2 located on the other side of the thin portion S2 attempts to contract (be displaced) toward the inside in the diameter direction. As a result, the surfaces of the protruding regions T1 and T2 can be arranged at positions closer to those of one perfect circle.

As shown in FIG. 6, the widths L2 in the circumferential direction of the recessed grooves G1, G2, and G3 are preferably the same value. In other words, in the circumferential direction, the angle range θ2 in which the recessed groove G1 (thin portion S1) is provided, the angle range θ2 in which the recessed groove G2 (thin portion S2) is provided, and the angle range θ2 in which the recessed groove G3 (thin portion S3) is provided are the same value.

According to this configuration, if focus is given to the protruding region T1, there will hardly be any difference between the force with which the thin portion S1 located on one side of the protruding region T1 attempts to contract (be displaced) toward the inner side in the radial direction and the force with which the thin portion S2 located on the other side of the protruding region T1 attempts to contract (be displaced) toward the inner side in the radial direction. Similarly, if focus is given to the protruding region T2, there will hardly be any difference between the force with which the thin portion S2 located on one side of the protruding region T2 attempts to contract (be displaced) toward the inner side in the radial direction and the force with which the thin portion S3 located on the other side of the protruding region T2 attempts to contract (be displaced) toward the inner side in the radial direction. As a result, the surfaces of the protruding regions T1 and T2 can be arranged at positions closer to those of one perfect circle.

As described above, in the present embodiment, a total of four recessed grooves G1, G2, G3, and G4 are included in the multiple recessed grooves 124. The interval L1 between the recessed grooves G1 and G2, the interval L1 between the recessed grooves G2 and G3, and the interval L1 between the recessed grooves G3 and G4 are all the same value, and furthermore, the interval L1 between the recessed grooves G4 and G1 is the same value as those intervals L1. The widths L2 in the circumferential direction of each of the recessed grooves G1, G2, G3, and G4 are the same value. When producing the bobbin 120, the force with which the thick portions R1, R2, R3, and R4 attempt to be displaced toward the inner side in the radial direction, and the force with which the thin portions S1, S2, S3, and S4 attempt to be displaced toward the inner side in the radial direction are balanced, and as a result, the surfaces of the protruding regions T1, T2, T3, and T4 can be arranged at positions closer to those of one perfect circle.

In the present embodiment, furthermore, the groove depths in the radial direction of each of the recessed grooves G1, G2, G3, and G4 are also the same, and the stress that occurs during production of the bobbin 120 is more balanced in the circumferential direction, and as a result, the surfaces in the protruding regions T1, T2, T3, and T4 can be arranged at positions closer to those of one perfect circle.

If the surfaces of the protruding regions T1 and T2 or the surfaces of all of the protruding regions T1, T2, T3, and T4 are arranged at positions closer to those of one perfect circle, the clearance between the inner circumferential surface 122 of the bobbin 120 and the outer circumferential surface 142 of the plunger 140 can be made smaller. The plunger 140 is held more stably by the bobbin 120, and the plunger 140 can slide stably inside of the bobbin 120 with an appropriate friction force. In this kind of case, the plunger 140 can move stably (with little rattling) inside of the bobbin 120, and thus the manner in which the valve body 150 comes into contact with the outflow port 132 is less likely to vary.

As shown in FIG. 4, the seal surface 151 of the valve body 150 is inclined in some cases. If the manner in which the seal surface 151 comes into contact with the outflow port 132 varies, variation is more likely to occur in the timing at which the outflow port 132 opens and the degree to which the outflow path of the fluid widens, and thus, in the present embodiment, the manner in which the seal surface 151 of the valve body 150 comes into contact with the outflow port 132 is effectively prevented from varying, and variations are effectively prevented from occurring in the timing at which the outflow port 132 opens and the degree to which the outflow path of the fluid widens. Accordingly, if the flow rate control valve 100A is operated under the same control conditions, hardly any variation occurs to such an extent that the internal pressure of the cuff decreases, and thus different characteristics are hardly ever exhibited each time measurement is performed, and it is possible to expect an improvement in the yield and an improvement in product quality due to a reduction of lot rejection.

As shown in FIG. 5, it is preferable that, in a case of drawing a straight line LL that is orthogonal to the pair of side walls 111 and 112 and passes through the axis CT of the bobbin 120, one of the multiple protruding regions T1 to T4 is arranged at a position intersecting the straight line LL. According to this configuration, for example, when the flow rate control valve 100A (or the blood pressure monitor 1 shown in FIG. 1) is installed such that the side walls 111 and 112 are horizontal, the protruding region (here, protruding region T2) can mainly receive the weight of the plunger 140 on its wide inner surface.

If the recessed grove G2 or the recessed groove G3 is arranged at a position intersecting the above-described straight line LL, when the flow rate control valve 100A (or the blood pressure monitor 1) is installed such that side walls 111 and 112 are horizontal, the weight of the plunger 140 does not act on the inner surfaces of the protruding regions T1 to T4 compared to the above-described case. Accordingly, in the case of considering enabling stable holding of the plunger 140 using the inner surfaces of the protruding regions T1 to T4 when the flow rate control valve 100A is installed such that the side walls 111 and 112 are horizontal, it is preferable that one of the protruding regions T1 to T4 is arranged at a position intersecting the straight line LL. It is more suitable that the central portion in the circumferential direction of the inner surface of any one of the protruding regions T1 to T4 intersects with the straight line LL.

Alternatively, in the case of considering enabling stable holding of the plunger 140 using the inner surfaces of the protruding regions T1 to T4 when the flow rate control valve 100A or the blood pressure monitor 1 shown in FIG. 1 is installed such that the side walls 111 and 112 are perpendicular to the gravity direction, one of the protruding regions T1 to T4 may be arranged at a position intersecting the straight line that is orthogonal to the straight line LL.

For example, in a state in which the main body 10 (FIG. 1) of the blood pressure monitor 1 is placed on a horizontal placement surface, one of the multiple protruding regions T1 to T4 of the flow rate control valve 100A is preferably located lower than all of the recessed grooves G1 to G4 in the gravity direction. It is more suitable that the central portion in the circumferential direction of the inner surface of any one of the protruding regions T1 to T4 is arranged at the lowest position in the gravity direction on the inner circumferential surface 122 of the bobbin 120. With these configurations, the plunger 140 can be held stably using the inner surfaces of the protruding regions.

COMPARATIVE EXAMPLE

Figure 7:
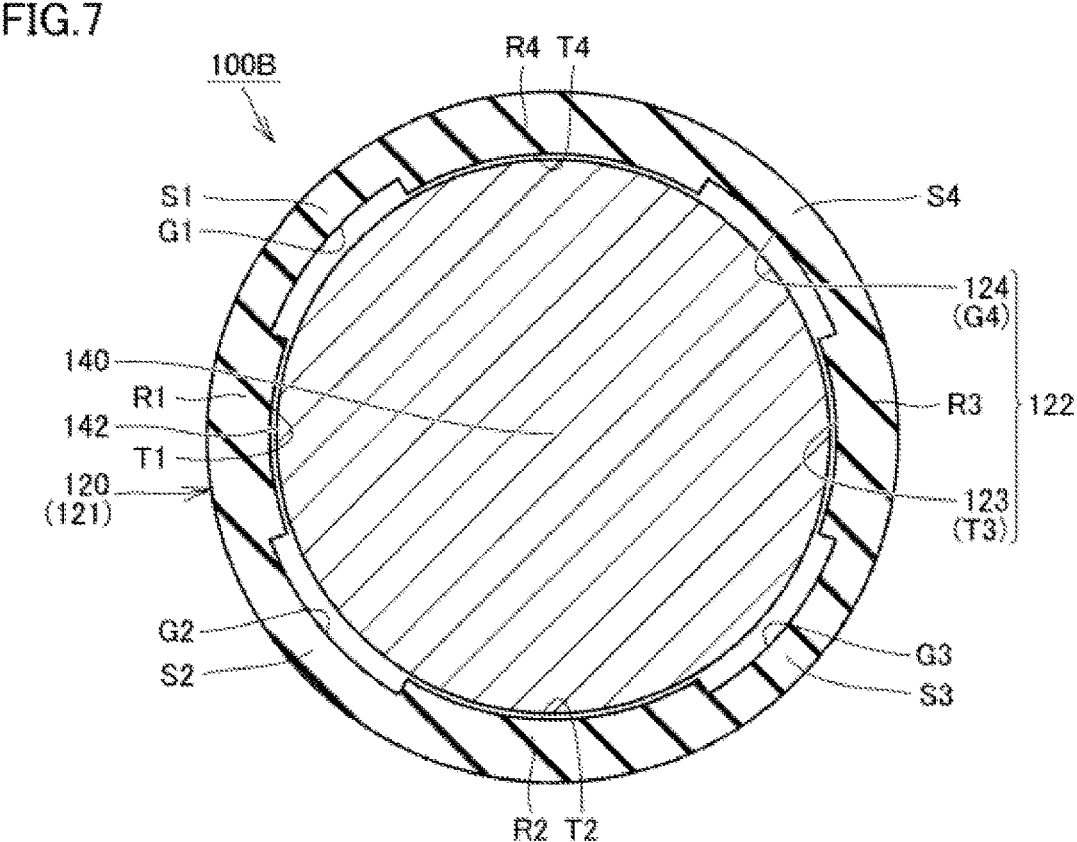
FIG. 7 is a cross-sectional diagram showing a bobbin and a plunger included in a flow rate control valve of a comparative example.
Figure 8:
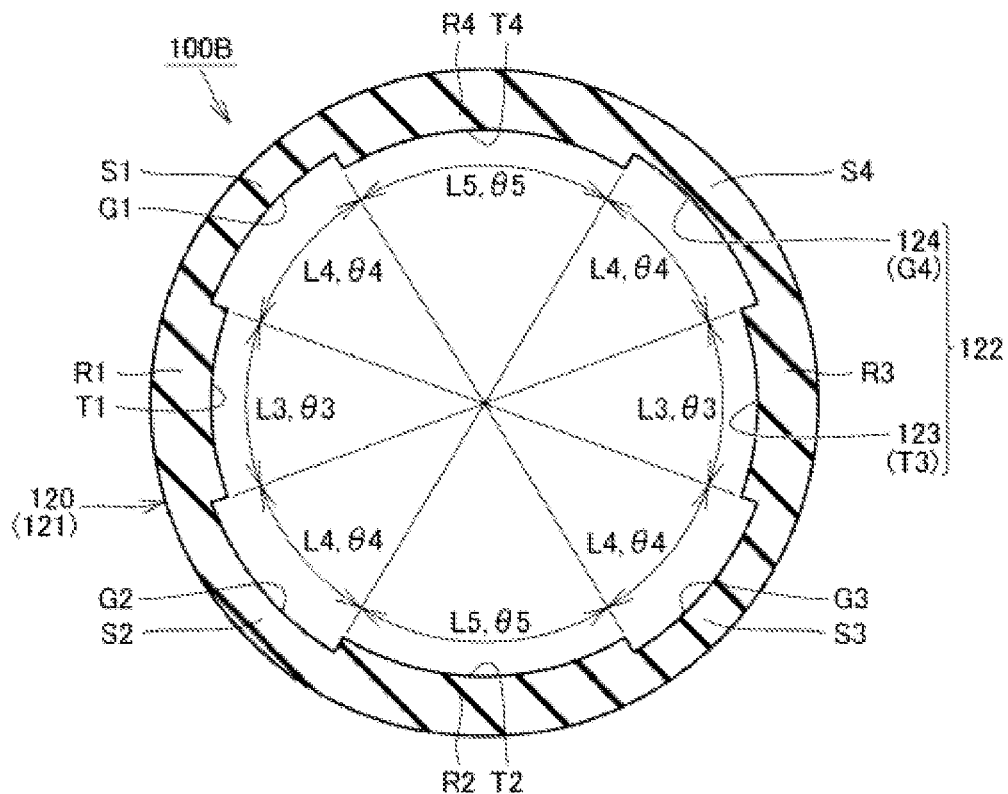
FIG. 8 is a cross-sectional diagram showing a bobbin included in a flow rate control valve of a comparative example.

FIG. 7 is a cross-sectional diagram showing a bobbin 120 and a plunger 140 included in a flow rate control valve 100B according to a comparative example. FIG. 8 is a cross-sectional diagram showing the bobbin 120 included in the flow rate control valve 100B.

As shown in FIGS. 7 and 8, in the comparative example, the widths L4 (angle ranges θ4) in the circumferential direction of each of the recessed grooves G1, G2, G3, and G4 are identical to each other, but an interval L3 between the recessed grooves G1 and G2 and an interval L5 between the recessed grooves G2 and G3 are different. Furthermore, the interval L5 between the recessed grooves G2 and G3 and the interval L3 between the recessed grooves G3 and G4 are different, and the interval L3 between the recessed grooves G3 and G4 and the interval L5 between the recessed grooves G4 and G1 are also different.

When producing the bobbin 120, the force with which the thick portions R1, R2, R3, and R4 attempt to be displaced toward the inner side in the radial direction, and the force with which the thin portions S1, S2, S3, and S4 attempt to be displaced toward the inner side in the radial direction are not balanced, and it is difficult for the surfaces of the protruding regions T1, T2, T3, and T4 to be arranged at positions closer to those of one perfect circle.

As shown in FIG. 7, for example, the flow rate control valve 100B is arranged such that the protruding region T2 (thick portion R2) among the protruding regions T1 to T4 is the lowest in the circumferential direction. In this case, the weight of the plunger 140 is mainly received by the inner surface of the protruding region T2.

Figure 9:
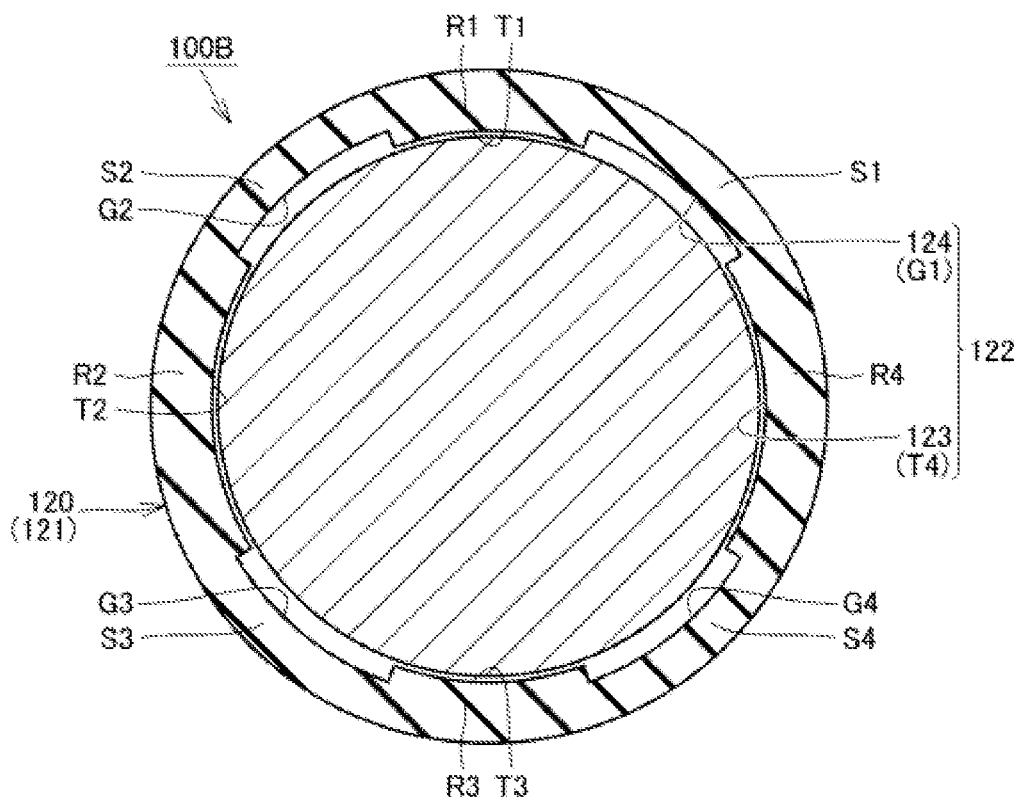
FIG. 9 is another cross-sectional diagram showing a bobbin and a plunger included in a flow rate control valve of a comparative example.

FIG. 9 is another cross-sectional diagram showing the bobbin 120 and the plunger 140 included in the flow rate control valve 100B. As shown in FIG. 9, the flow rate control valve 100B is arranged such that the protruding region T3 (thick portion R3) among the protruding regions T1 to T4 is the lowest in the circumferential direction. In this case, the weight of the plunger 140 is mainly received by the inner surface of the protruding region T3.

In the flow rate control valve 100B of the comparative example, the surface area of the protruding region T2 and the surface area of the protruding region T3 are different, and depending on the method of installing the flow rate control valve 100B, the frictional force that occurs between the plunger 140 and the bobbin 120 is likely to vary. Even if a flow rate control valve is operated with the same control conditions, depending on the method of installing the flow rate control valve 100B, variation will occur to such an extent that the internal pressure of the cuff decreases, and it is conceivable that different characteristics will be displayed each time measurement is performed.

In contrast to this, in the above-described Embodiment 1, the surface areas of the protruding regions T1 to T4 are the same. The outer circumferential surface 142 of the plunger 140 and the inner circumferential surface 122 of the bobbin 120 have rotationally symmetrical shapes and are hardly influenced by the method of installing the flow rate control valve 100A when the flow rate control is operated under the same conditions, and thus no variation occurs to such an extent that the internal pressure of the cuff decreases, and characteristics that are different each time measurement is performed are effectively prevented from being exhibited.

Embodiment 2

Figure 10:
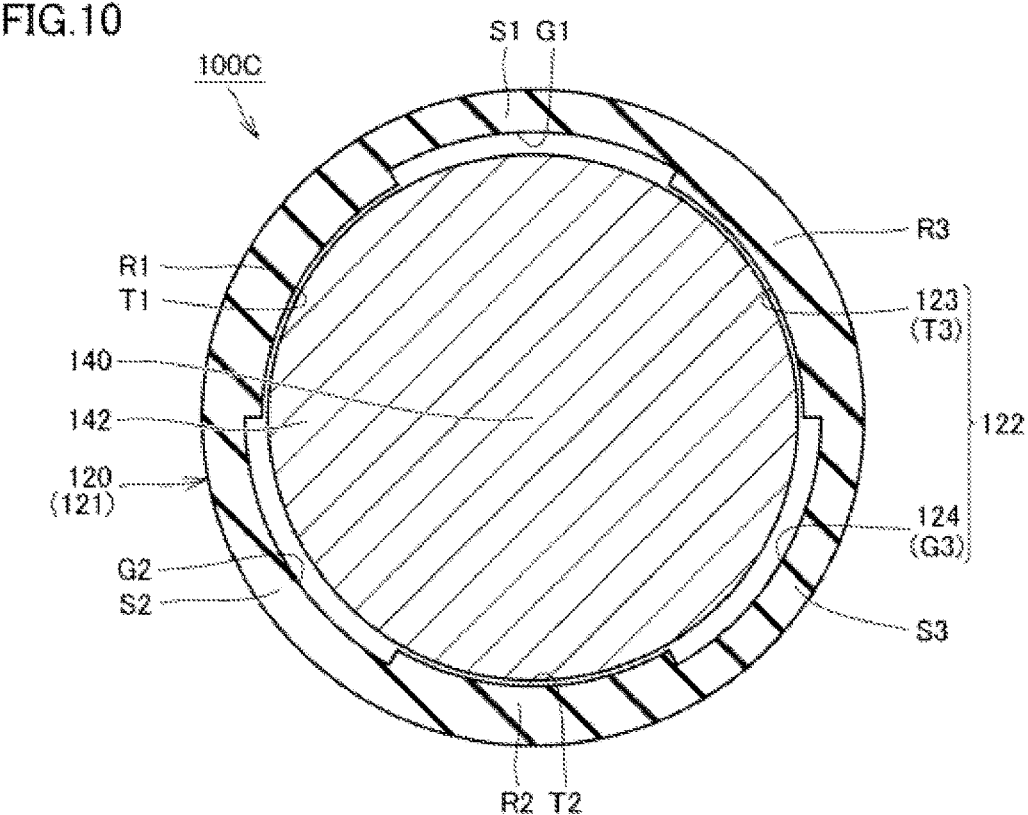
FIG. 10 is a cross-sectional diagram showing a bobbin and a plunger included in a flow rate control valve of Embodiment 2.

FIG. 10 is a cross-sectional diagram showing a bobbin 120 and a plunger 140 included in a flow rate control valve 100C according to Embodiment 2. Embodiment 1 and Embodiment 2 differ in the following respects.

In the bobbin 120 of the flow rate control valve 100C, a total of three recessed grooves G1, G2, and G3 are included as the multiple recessed grooves 124, and a total of three protruding regions T1, T2, and T3 are included as the multiple protruding regions 123. In the present embodiment as well, the interval between the recessed grooves G1 and G2 and the interval between the recessed grooves G2 and G3 are the same, and furthermore, the interval between the recessed grooves G2 and G3 is the same as those intervals as well. According to this configuration as well, it is possible to obtain actions and effects similar to those of the above-described Embodiment 1.

Embodiment 3

Figure 11:
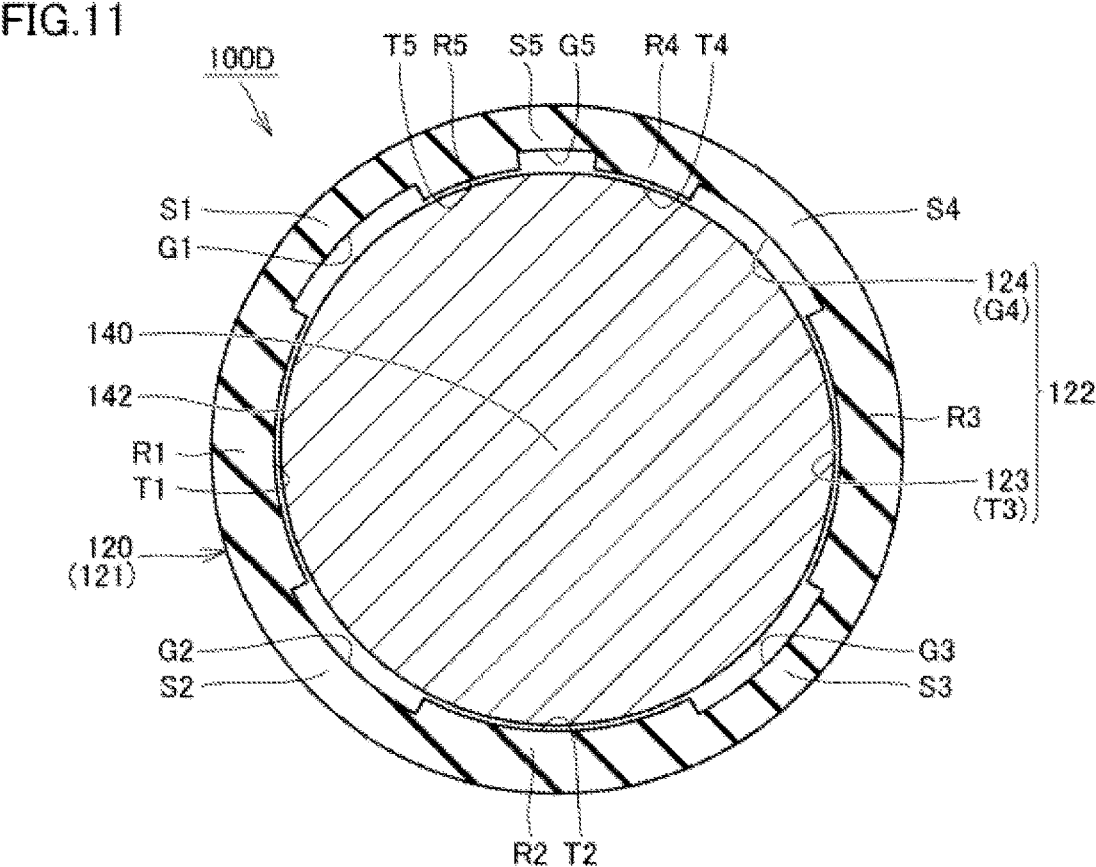
FIG. 11 is a cross-sectional diagram showing a bobbin and a plunger included in a flow rate control valve of Embodiment 3.

FIG. 11 is a cross-sectional diagram showing a bobbin 120 and a plunger 140 included in a flow rate control valve 100D according to Embodiment 3. Embodiment 1 and Embodiment 3 differ in the following respects.

In the bobbin 120 of the flow rate control valve 100D, the multiple recessed grooves 124 further include a recessed groove G5 (fifth groove) that is formed between the recessed groove G1 and the recessed groove G4.

If focus is given to the thin portion S1, there will be a difference between the force with which the thick portion R1 located on one side of the thin portion S1 attempts to contract (be displaced) toward the inside in the diameter direction and the force with which the thick portion R5 located on the other side of the thin portion S1 attempts to contract (be displaced) toward the inside in the diameter direction. The same follows for the case of focusing on the thin portion S4 and the case of focusing on the thick portions R4 and R5.

However, if focus is given to the thin portion S2, there is hardly be any difference between the force with which the thick portion R1 located on one side of the thin portion S2 attempts to contract (be displaced) toward the inside in the diameter direction and the force with which the thick portion R3 located on the other side of the thin portion S2 attempts to contract (be displaced) toward the inside in the diameter direction. The same follows for the case of focusing on the thin portion S3 and the case of focusing on the thick portions R1, R2, and R3. When producing the bobbin 120, the forces with which these portions attempt to be displaced toward the inner side in the radial direction are balanced, and as a result, the surfaces of the protruding regions T1, T2, and T3 can be arranged at positions closer to those of one perfect circle.

Embodiment 4

Figure 12:
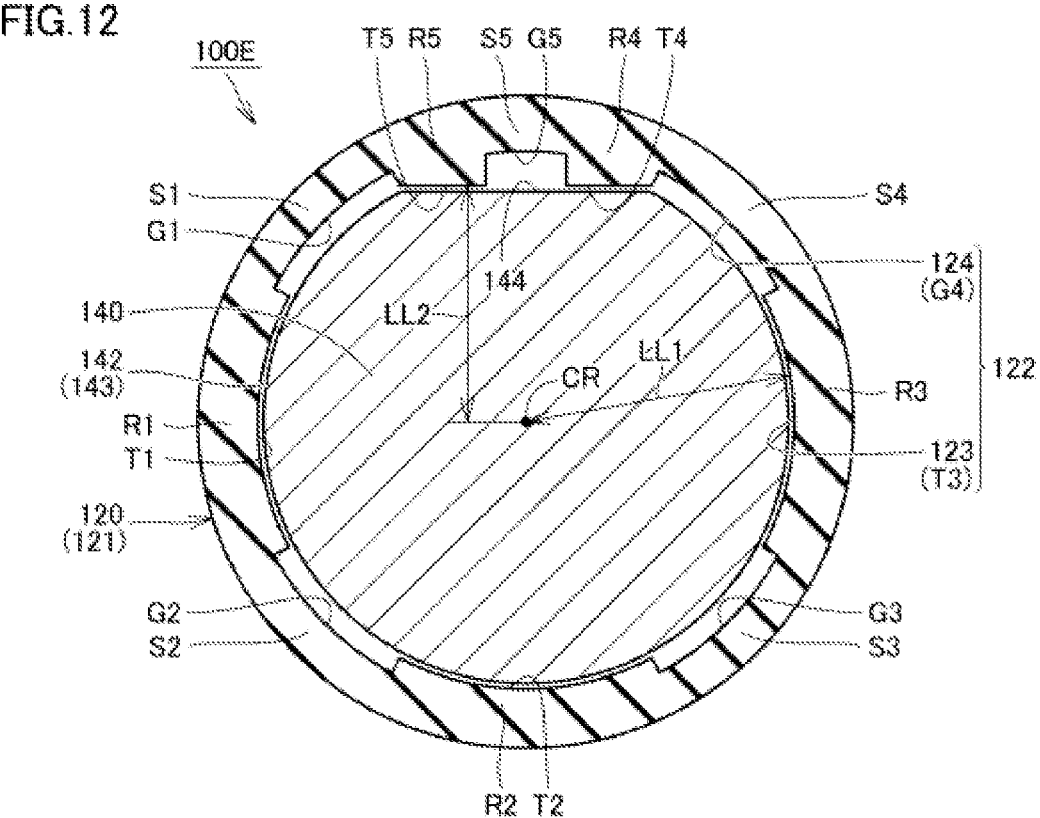
FIG. 12 is a cross-sectional diagram showing a bobbin and a plunger included in a flow rate control valve of Embodiment 4.
Figure 13:
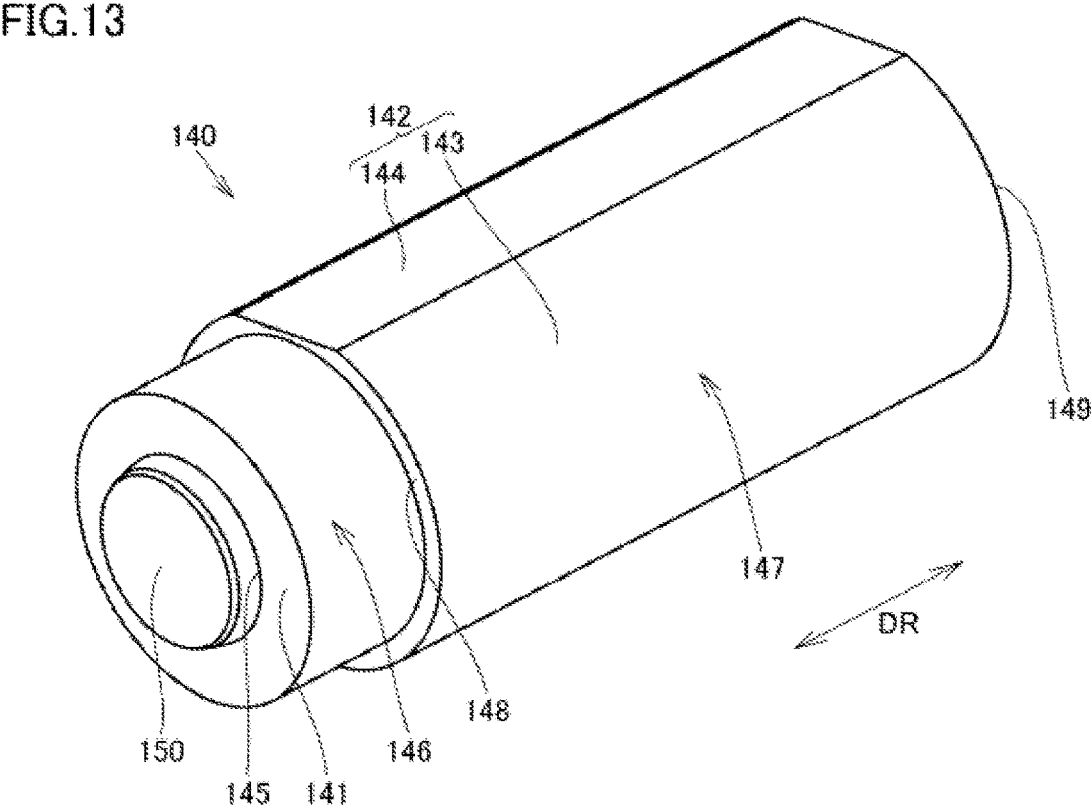
FIG. 13 is a perspective view showing a plunger included in a flow rate control valve of Embodiment 4.

FIG. 12 is a cross-sectional diagram showing a bobbin 120 and a plunger 140 included in a flow rate control valve 100E according to Embodiment 4. FIG. 13 is a perspective view showing the plunger 140 included in the flow rate control valve 100E. Embodiment 3 and Embodiment 4 differ in the following respects.

As shown in FIGS. 12 and 13, in the flow rate control valve 100E, the outer circumferential surface 142 of the plunger 140 includes a circumferential surface region 143 that extends along the circumferential direction, and an engagement region 144 that extends in a direction parallel to the axial direction of the plunger 140 and has a flat surface shape.

As shown in FIG. 12, the protruding regions T4 and T5 provided on the bobbin 120 protrude toward the inner side compared to the case of Embodiment 3. In other words, the distance LL1 between the center of curvature CR of the protruding regions T1 to T3 and the protruding regions T4 and T5 is shorter compared to the distance LL2 between the center of curvature CR of the protruding regions T1 to T3 and the protruding regions T1 to T3.

In the state in which the plunger 140 is arranged inside of the bobbin 120, the above-described engagement region 144 opposes the pair of protruding regions T4 and T5 located on both sides of the recessed groove G5 in the circumferential direction, and thus rotation of the plunger 140 inside of the bobbin 120 is prevented due to the engagement region 144 and the pair of protruding regions T4 and T5 engaging with each other. That is, in the present embodiment, a rotation prevention mechanism that prevents the plunger 140 from rotating inside of the bobbin 120 is constituted by the outer circumferential surface 142 of the plunger 140 and the inner circumferential surface 122 of the bobbin 120.

As stated in Embodiment 1, the outflow port 132 is closed due to the seal surface 151 of the valve body 150 (see FIG. 4 and the like) provided on the end portion of the plunger 140 coming into contact or close contact with the outflow port 132 (specifically, the edge portion forming the outflow port 132 of the core 130; the same follows hereinafter). When the plunger 140 rotates with respect to the bobbin 120, the manner in which the seal surface 151 of the valve body 150 comes into contact with the outflow port 132 also varies.

If the manner in which the seal surface 151 of the valve body 150 comes into contact with the outflow port 132 varies, variation is more likely to occur in the timing at which the outflow port 132 opens and the degree to which the outflow path of the fluid widens. The seal surface 151 and the outflow port 132 have manufacturing errors in some cases. For example, if the nozzle portion 131 of the core 130 is formed through a turning process, it is also possible that the outflow port 132 is misaligned from the designed position (center position) depending on the processing accuracy, or minute scratches or chipping occurs on the circumferential edge portion of the outflow port 132 due to post-processing. As shown in FIG. 4, the seal surface 151 of the valve body 150 is inclined in some cases. In these cases, if the manner in which the seal member 151 comes into contact with the outflow port 132 varies, variation is more likely to occur in the timing at which the outflow port 132 opens and the degree to which the outflow path of the fluid widens.

In contrast to this, in the present embodiment, the plunger 140 is prevented from rotating with respect to the bobbin 120 inside of the bobbin 120 due to the engagement region 144 and the protruding regions T4 and T5 engaging with each other. As a result, the manner in which the seal surface 151 of the valve body 150 comes into contact with the outflow port 132 is effectively prevented from varying, and variation is effectively prevented from occurring in the timing at which the outflow port 132 opens and the degree to which the outflow path of the fluid widens. Accordingly, if the flow rate control valve 100E is operated under the same control conditions, hardly any variation occurs to such an extent that the internal pressure of the cuff decreases, and thus different characteristics are hardly ever exhibited each time measurement is performed, and it is possible to expect an improvement in the yield and an improvement in product quality due to a reduction of lot rejection.

As shown in FIG. 13, the engagement region 144 of the present embodiment is provided so as to extend over the entirety in the axial direction of the large diameter portion 147, to reach the end portion 149 of the large diameter portion 147 from the level difference 148 in the axial direction.

Figure 14:
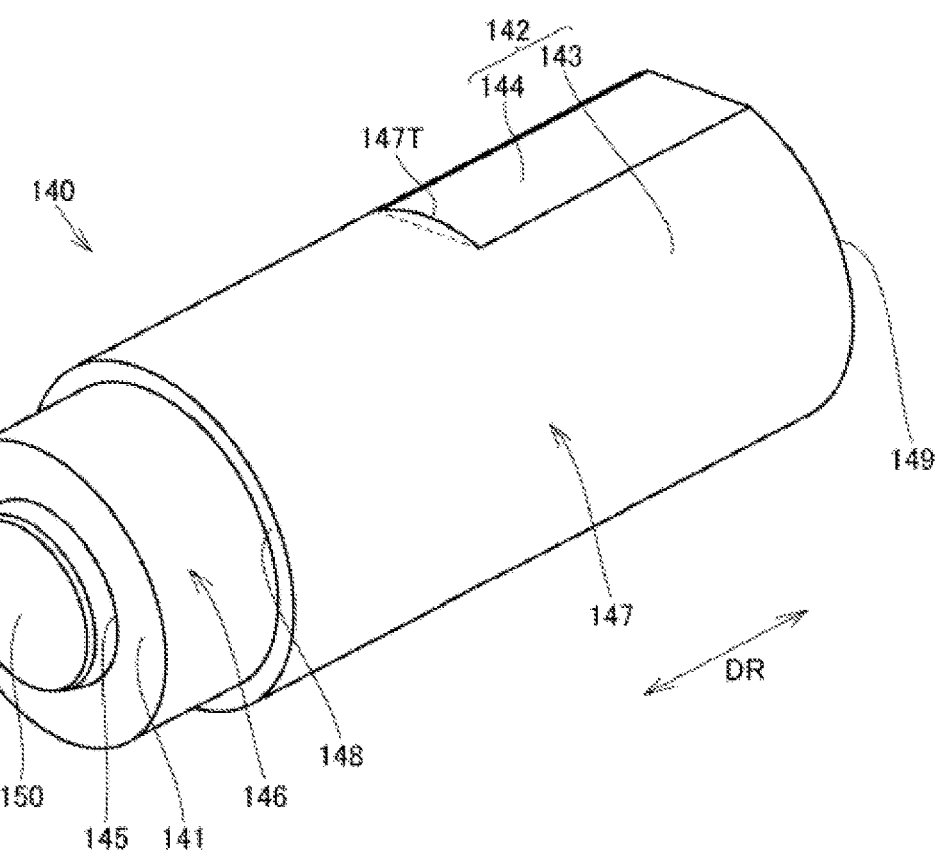
FIG. 14 is a perspective view showing a plunger included in a flow rate control valve of a modified example of Embodiment 4.

As shown in FIG. 14, the engagement region 144 may be provided only at a portion in the axial direction of the large diameter portion 147. The engagement region 144 shown in FIG. 14 is provided so as to reach the end portion 149 of the large diameter portion 147 from an intermediate portion 147T in the axial direction of the large diameter portion 147. The engagement region 144 having this kind of shape can easily be provided on the plunger 140 through pultrusion molding. Conversely, the engagement region 144 may be provided so as to reach the level difference 148 from the intermediate portion 147T in the axial direction of the large diameter portion 147.

In the embodiments and modified examples described above, a case in which the fluid being subjected to flow rate control was compressed air was described as an example, but the target of application of the content disclosed above is not limited thereto, and the fluid subjected to flow rate control may be a high-pressure gas other than compressed air, or a liquid in a compressed environment, or the like. Also, the characteristic configurations indicated in the above-described embodiments and modified examples of the present invention can of course be combined with each other as needed.

Although embodiments have been described above, the content disclosed above is in all respects exemplary and not limiting. The technical scope of the present invention is indicated by the claims, and meanings equivalent to the claims and all modifications within the scope are intended to be included therein.

REFERENCE SIGNS LIST

10 Main body
20 Control unit
21 Display unit
22 Memory unit
23 Operation unit
24 Power source unit
30 Compression air system component
31 Pressure pump
33 Pressure sensor
34 Pressure pump drive circuit
35 Flow rate control valve drive circuit
36 Oscillation circuit
40 Cuff
41 Outer cover
42 Compression air bladder
50 Air tube
100A, 100B, 100C, 100D, 100E Flow rate control valve
110 Frame
111, 112 Side wall
113, 127, 128 End wall
114 Base
120 Bobbin
121 Cylindrical portion
122 Inner circumferential surface
123, T1, T2, T3, T4, T5 Protruding region
124, G1, G2, G3, G4, G5 Recessed groove
129 Bottom portion
130 Core
131 Nozzle portion
132 Outflow port
140 Plunger
141 End surface
142 Outer circumferential surface
143 Circumferential surface region
144 Engagement region 145 Containing recess
146 Small diameter portion
147 Large diameter portion
147T Intermediate portion
148 Level difference
149 End portion
150 Valve body
151 Seal surface
152 Solenoid coil
154, 156 Connection terminal
160 Spring
CR, CT Center of curvature (axial center)
DR Arrow
L1, L3, L5 Interval
L2, L4 Width
LL Straight line
LL1, LL2 Distance
R1, R2, R3, R4, R5 Thick portion
S1, S2, S3, S4 Thin portion

The invention claimed is:

1. A flow rate control valve capable of variably controlling a flow rate of a fluid, comprising:
a solenoid coil for generating a magnetic flux;
a bobbin around which the solenoid coil is wound;
a plunger that is arranged inside of the bobbin and is configured to move in an axial direction due to the magnetic flux formed by the solenoid coil;
a core in which an outflow port through which the fluid is to pass is formed; and
a valve body that is provided at an end portion of the plunger so as to oppose the outflow port, and is configured to open and close the outflow port by separating from and coming into contact with the core,
wherein on an inner circumferential surface of the bobbin,
a plurality of protruding regions that extend in a direction parallel to the axial direction of the plunger and a plurality of recessed grooves that form flow paths for the fluid when the valve is open are provided side by side alternatingly in a circumferential direction,
the plurality of recessed grooves include a first recessed groove, a second recessed groove, a third recessed groove, and a fourth groove that are arranged side by side sequentially in the circumferential direction,
an interval in the circumferential direction between the first recessed groove and the second recessed groove, an interval in the circumferential direction between the second recessed groove and the third recessed groove, and an interval in the circumferential direction between the third recessed groove and the fourth recessed groove are the same,
the plurality of recessed grooves further include a fifth recessed groove formed between the first recessed groove and the fourth recessed groove,
an outer circumferential surface of the plunger includes a circumferential surface region that extends in a circumferential direction, and an engagement region that extends in a direction parallel to the axial direction of the plunger and has a flat surface shape, and
in a state in which the plunger is arranged inside of the bobbin, the engagement region opposes a pair of the protruding regions located on both sides of the fifth groove in the circumferential direction, and the plunger is prevented from rotating inside of the bobbin due to the engagement region and the pair of the protruding regions engaging with each other.

2. The flow rate control valve according to claim 1, wherein the widths in the circumferential direction of the first recessed groove, the second recessed groove, and the third recessed groove are the same.

3. The flow rate control valve according to claim 1, wherein groove depths in a radial direction of the first recessed groove, the second recessed groove, the third recessed groove, and the fourth recessed groove are the same.

4. The flow rate control valve according to claim 1, further comprising
a frame having a pair of side walls,
wherein the bobbin and the plunger are arranged between the pair of side walls, and
if a straight line that is orthogonal to the pair of side walls and passes through an axial center of the bobbin is drawn, the protruding region is arranged at a position intersecting the straight line.

5. The flow rate control valve according to claim 1, wherein
the plunger includes a small diameter portion inside of which the valve body is arranged, and a large diameter portion that is arranged on a side opposite to the side on which the valve body is arranged with respect to the small diameter portion, in the axial direction, and
the engagement region is provided only in the large diameter portion.

6. The flow rate control valve according to claim 5, wherein the engagement region is provided only on a portion in the axial direction of the large diameter portion.

7. A blood pressure information measurement apparatus, comprising the flow rate control valve according to claim 1, as a discharge valve for reducing internal pressure of a compression fluid bladder for compressing a living body.

8. The blood pressure information measurement apparatus according to claim 7, wherein if the flow rate control valve is provided in a main body of the blood pressure information measurement apparatus, in a state in which the main body is placed on a horizontal placement surface, one of the plurality of protruding regions of the flow rate control valve is located lower than all of the recessed grooves in a gravity direction.

* * * * *